(12) United States Patent
Vergauwen et al.

(10) Patent No.: US 12,371,569 B2
(45) Date of Patent: Jul. 29, 2025

(54) LOW ENDOTOXIN GELATIN-(METH)ACRYLOYL

(71) Applicant: ROUSSELOT BV, Ghent (BE)

(72) Inventors: Bjorn Vergauwen, Ghent (BE); Elke De Clerck, Ghent (BE)

(73) Assignee: ROUSSELOT BV, Ghent (BE)

( * ) Notice: Subject to any disclaimer, the term of this patent is extended or adjusted under 35 U.S.C. 154(b) by 0 days.

(21) Appl. No.: 17/917,774

(22) PCT Filed: May 19, 2021

(86) PCT No.: PCT/EP2021/063257
§ 371 (c)(1),
(2) Date: Oct. 7, 2022

(87) PCT Pub. No.: WO2021/233981
PCT Pub. Date: Nov. 25, 2021

(65) Prior Publication Data
US 2023/0133041 A1    May 4, 2023

(30) Foreign Application Priority Data
May 19, 2020   (BE) .................................. 2020/5347

(51) Int. Cl.
| C08L 89/06 | (2006.01) |
| A61L 27/22 | (2006.01) |
| A61L 27/52 | (2006.01) |
| C08J 3/075 | (2006.01) |

(52) U.S. Cl.
CPC ............ *C08L 89/06* (2013.01); *A61L 27/222* (2013.01); *A61L 27/52* (2013.01); *C08J 3/075* (2013.01); *C08J 2389/06* (2013.01); *C08L 2203/16* (2013.01)

(58) Field of Classification Search
CPC .... C08L 89/06; C08L 2203/16; A61L 27/222; A61L 27/52; C08J 3/075; C08J 2389/06; C08J 5/18; A61K 9/06; A61K 47/42; C08H 1/06
See application file for complete search history.

(56) References Cited

U.S. PATENT DOCUMENTS

| 10,155,805 | B2 | 12/2018 | Olijve et al. |
| 2011/0168635 | A1* | 7/2011 | Bender ................. C08B 37/006 |
| | | | 210/663 |
| 2017/0239356 | A1 | 8/2017 | Kamiya et al. |
| 2019/0022280 | A1 | 1/2019 | Khademhosseini et al. |

FOREIGN PATENT DOCUMENTS

| JP | 2019-526326 A | 9/2019 |
| KR | 10-2018-0085677 A | 7/2018 |
| WO | WO 2009/154440 A1 | 12/2009 |
| WO | WO 2015/159995 A1 | 10/2015 |
| WO | WO 2018/033739 A1 | 2/2018 |
| WO | WO 2019/219828 A1 | 11/2019 |

OTHER PUBLICATIONS

Groen et al., "In Vitro Response of Mesenchymal Stromal Cells and Peripheral Blood Mononuclear Cells to High- And Low- Endotoxin Gelatine Methacryloyl Hydrogels", Osteoarthritis and Cartilage, 2020, 28(Suppl 1): S523-S524, Abstract 790.
Hoch et al., "Chemical Tailoring of Gelatin to Adjust its Chemical and Physical Properties for Functional Bioprinting", Journal of Materials Chemistry B, 2013, 1(41): 5675-5685.
Shirahama et al., "Precise Tuning of Facile One-Pot Gelatin Methacryloyl (GelMA) Synthesis," Scientific Reports, Aug. 9, 2016, 6: 31036.
International Search Report and Written Opinion for PCT International Patent Application No. PCT/EP2021/063257, dated Aug. 27, 2021.
International Preliminary Report on Patentability for PCT International Patent Application No. PCT/EP2021/063257, dated Dec. 1, 2022.
Pahoff et al., "Effect of gelatin source and photoinitiator type on chondrocyte redifferentiation in gelatin methacryloyl-based tissue-engineered cartilage constructs", Journal of Materials Chemistry B, Jan. 1, 2019, 7(10): 1761-1772.

* cited by examiner

*Primary Examiner* — Jessica Worsham
(74) *Attorney, Agent, or Firm* — Lathrop GPM LLP; Judith Stone-Hulslander; James Velema

(57) ABSTRACT

The present invention relates to methacryloyl-gelatin and acryloyl-gelatin with low pyrogenic activity, in particular with low lipopolysaccharide content. The (meth)acryloyl-gelatin is further characterized by low (meth)acrylic acid content. The invention further relates to methods for preparing said (meth)acryloyl-gelatin, which do not require a dialysis step. The invention further relates to hydrogels comprising this (meth)acryloyl-gelatin, as well as uses thereof for tissue-engineering applications, and as bio-ink or bio-resin.

10 Claims, 1 Drawing Sheet

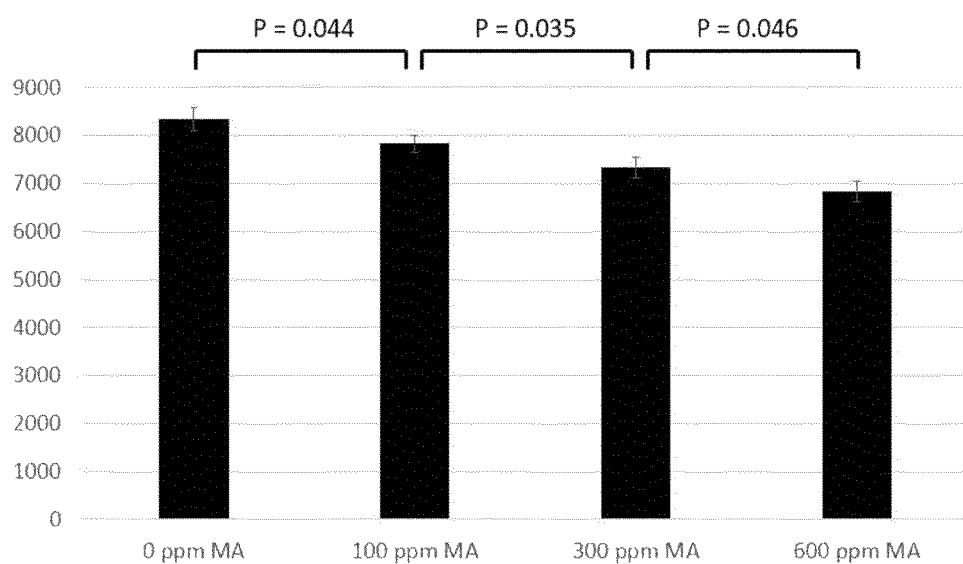

LOW ENDOTOXIN GELATIN-(METH)ACRYLOYL

RELATED APPLICATIONS

The instant application is a 35 U.S.C. § 371 filing of International Patent Application No. PCT/EP2021/063257, filed May 19, 2021, which claims priority to Belgian Patent Application No. 2020/5347, filed May 19, 2020, the entire contents of which are incorporated herein by reference for all purposes.

TECHNICAL FIELD

The application generally relates to chemically functionalized gelatin, in particular methacryloyl-gelatin and acryloyl-gelatin. More particularly, the invention relates to methacryloyl-gelatin and acryloyl-gelatin with low pyrogenic activity, in particular low lipopolysaccharide content, hydrogels comprising said methacryloyl-gelatin or acryloyl-gelatin, methods for preparing said methacryloyl-gelatin and acryloyl-gelatin and uses thereof.

BACKGROUND

Reconstruction of functional biological tissue, biological implants, and cell-based multi-organ models for clinical, diagnostic or pharmaceutical research receive high attention. Hydrogels have emerged as leading candidates for various tissue engineering applications due to their similarity with the native extracellular matrix.

Gelatin hydrogels are particularly attractive because of their biocompatibility and biodegradability. Gelatin is produced by the partial hydrolysis of collagen, the most abundant protein in the body and the most prevalent molecule of the extracellular matrix. The abundant presence of the cell-recognition sequence Arginine-Glycine-Aspartic acid (RGD) facilitates attachment of cells to gelatin promoting their spreading and proliferation. These cell-matrix interactions are crucial for the organization of complex tissue. Thanks to the long history of gelatin as a trusted excipient within the pharmaceutical industry, it meets the highest standards of safety and regulatory compliance. Furthermore, the presence of free amino groups, hydroxyl groups and carboxylate groups enable chemical modification to achieve desired properties for specific applications.

Gelatin hydrogels are fabricated by crosslinking of gelatin polymers, either without prior modification or after functionalization of their side groups. The addition of functional groups to the gelatin backbone is a crosslinking strategy with a high degree of control over hydrogel design and properties. The most extensively used and studied modification for crosslinking gelatin is methacryloylation. MA-modified gelatin is generally referred to as gelMA. An alternative to the well-established methacryloyl-gelatin is acryloyl-gelatin (Billiet et al. 2013 "Quantitative Contrasts in the Photopolymerization of Acrylamide and Methacrylamide-Functionalized Gelatin Hydrogel Building Blocks" Macromolecular Bioscience 13:1531-45). Depending on the degree of (meth)acryloylation and the polymer concentration, the physical properties (crosslinking density, swelling and stiffness) of the gelatin-(meth)acryloyl hydrogels can be tailored, which makes this material a versatile platform for various tissue engineering applications. The crosslinking is initiated by radicals which are generated by UV or visible light depending on the photo-initiator used (e.g. Irgacure® 2959 or lithium phenyl-2,4,6-trimethylbenzoylphosphinate (LAP)).

One of the major drawbacks of gelatin-based hydrogels for (bio)medical applications is the presence of endotoxins (also referred to herein as lipopolysaccharides) in traditionally manufactured gelatin. Endotoxins are large, highly immunogenic molecules and the major component of the outer membrane of gram-negative bacteria. They are highly heat resistant, making them difficult to inactivate. When exposed to the immune system, endotoxins initiate an immune response, which can lead to tissue inflammation, increased sensitivity to other allergens, and the risk for fatal shock. Most research is currently conducted with gelMA that is based on gelatin with high endotoxin levels.

Traditionally manufactured gelatin can also be contaminated by microbial components other than endotoxins, some of which can, like endotoxins, cause an adverse immune response in humans. Non-endotoxin pyrogens include, for example, substances such as lipoteichoic acid (LTA) originating from Gram-positive bacteria, and other compounds originating from fungi, yeast, viruses, bacteria, and parasites (Hasiwa et al. (2013) "Evidence for the detection of non-endotoxin pyrogens by the whole blood monocyte activation test. ALTEX 30:169-208). These non-endotoxin pyrogens, and preferably pyrogens or Pathogen-Associated Molecular Patterns (PAMPs) in general, should also be kept to a minimum for (bio)medical applications of gelatin-based hydrogels to prevent unwanted side effects upon activation of innate immune receptors.

In addition, during the functionalization and crosslinking of gelatin to gelatin hydrogel, a number of reagents are used. Residues of reagents and reaction products can be present in the gelMA. For instance, upon reacting gelatin with methacrylic anhydride, methacrylic anhydride (MAAH) and/or methacrylic acid (MAA) can be present in the gelMA, which are considered hazardous. MAA may cause adverse effects at the site of application, depending on the concentration and frequency or time of exposure. The undiluted acid was shown to cause skin and eye corrosion and respiratory tract lesions by SIDS Initial Assessment Profile (SIAM 11, 2001). Unreacted methacrylic anhydride and methacrylic acid can be removed from the reaction mixture by dialysis against distilled water. Typically, dialysis is performed for one week, albeit shorter and longer periods of dialysis are also envisaged herein. This time-consuming step is therefore not efficient for large-scale production of gelMA. Furthermore, during this (week of) dialysis, the risk for microbial contamination and gelatin degradation increases and overall it complicates the process.

For (bio)medical applications of gelatin-based hydrogels, there is a need for biocompatible (meth)acryloyl gelatin (e.g. non-toxic to biological tissue and non-immunogenic), which allows to tailor hydrogels with desired mechanical properties (for example, strength and elasticity). There is also a need for manufacturing such (meth)acryloyl gelatin by an efficient process allowing production at industrial scale.

SUMMARY OF THE INVENTION

The present invention solves one or more of the above described problems of the prior art. In particular, methacryloyl-gelatin and acryloyl-gelatin are provided that have a low pyrogen content, in particular a low endotoxin content, and low contamination of methacrylic acid or acrylic acid. The (meth)acryloyl-gelatin has improved biocompatibility due to the low pyrogen content, in particular the low endotoxin content. The (meth)acrylyolyl-gelatin of the present invention is particularly useful for crosslinking due to the low contamination with methacrylic acid or acrylic acid, which is shown to interfere with the crosslinking process. Also advantageously, the (meth)acryloyl-gelatin can be prepared by a simple manufacturing process that does not require a (lengthy) dialysis step.

The present invention is in particular captured by any one or any combination of one or more of the below numbered aspects and embodiments (i) to (xvi) wherein:

(i) Gelatin modified with a methacryloyl group or an acryloyl group, having a lipopolysaccharide content of less than 100 EU/g, preferably less than 50 EU/g, more preferably less than 20 EU/g, even more preferably less than 10 EU/g, even more preferably less than 5 EU/g, even more preferably less than 2 EU/g, most preferably less than 1 EU/g and comprising less than 30 ppm of methacrylic acid or acrylic acid, wherein the methacrylic acid or acrylic acid content is determined on a sample of the gelatin dissolved in water, or comprising less than 100 ppm of methacrylic acid or acrylic acid, wherein the methacrylic acid or acrylic acid content is determined on a sample of the gelatin dissolved in 50 mM phosphate buffer, pH 9.5.

(ii) Gelatin according to (i), having a low content of pyrogens from Gram+ bacteria, pyrogens from flagellated bacteria, single-stranded viral RNA and bacterial DNA rich in unmethylated CpG motifs, preferably a low content of pyrogens from Gram+ bacteria and from flagellated bacteria, more preferably a low content of pyrogens from Gram+bacteria.

(iii) Gelatin according to (i) or (ii), wherein said gelatin is type A gelatin.

(iv) Gelatin according to any one of (i) to (iii), having a degree of methacrylamide substitution or acrylamide substitution of between 20% and 100%, preferably between 50% and 100%, more preferably between 80% and 100%, and a degree of methacrylate substitution of less than 10%.

(v) Gelatin according to any one of (i) to (iv), wherein said gelatin is further modified with an acetyl group or moiety, a phenol group or moiety, a thiol group or moiety, a norbornene group or moiety, a tetrazine group or moiety, an azide group or moiety, a furan group or moiety, or any combination thereof.

(vi) Hydrogel comprising a gelatin modified with a methacryloyl group or an acryloyl group according to any one of (i) to (v), and a cross-linking agent.

(vii) A film comprising a hydrogel according to (vi).

(viii) Method for preparing gelatin modified with a methacryloyl or acryloyl according to any one of (i) to (v), comprising the steps of:
a) modifying gelatin with a methacryloyl group or an acryloyl group by reacting gelatin with methacrylanhydride or acrylanhydride;
b) lowering the pH of the reaction medium to a value between 2.0 and 4.0, preferably between 2.0 and 3.5 or between 3 and 4, more preferably between 3.0 and 3.5;
c) adding 0.01-1.5 w/w % of a micelle-forming surfactant to the acidic reaction medium;
d) contacting the medium of step c) with a solid adsorbent;
e) separating the solid adsorbent of step d) from the medium; and
f) recovering the medium comprising the methacryloyl gelatin or the gelatin-acryloyl.

(ix) Method for preparing gelatin modified with a methacryloyl group or an acryloyl group according to any one of (i) to (v), comprising the steps of:
a) modifying gelatin with a methacryloyl group or an acryloyl group by reacting gelatin with methacrylanhydride or acrylanhydride;
$b_1$) lowering the pH of the reaction medium to a value between 4.0 and 9.0, preferably between 4.0 and 6.0, more preferably between 4.0 and 6.0, even more preferably between 4.5 and 5.5;
c) adding 0.01-1.5 w/w % of a micelle-forming surfactant to the reaction medium;
$b_2$) lowering the pH of the medium of step c) to a value between 2.0 and 4.0, preferably between 3.0 and 4.0, more preferably between 3.0 and 3.5;
d) contacting the medium of step $b_2$) with a solid adsorbent;
e) separating the solid adsorbent of step d) from the medium; and
f) recovering the medium comprising the methacryloyl gelatin or the gelatin-acryloyl.

(x) The method according to (viii) or (ix), wherein the method is free of a dialysis step.

(xi) The method according to any one of (viii) to (x), wherein said micelle-forming surfactant comprises a non-ionic surfactant, preferably wherein the surfactant is Triton X-100 or Triton X-102, or mixtures thereof.

(xii) The method according to any one of (viii)) to (xi), wherein said solid adsorbent is a hydrophobic adsorbent, preferably activated carbon.

(xiii) The method according to any one of (viii) to (xii), further comprising a step of drying the medium comprising the methacryloyl gelatin or the gelatin-acryloyl.

(xiv) Gelatin according to any one of (i) to (v) or a hydrogel according to (vi) for use in medicine.

(xv) In vitro or ex vivo use of gelatin according to any one of (i) to (v) or a hydrogel according to (vi) for manufacturing a biological construct such as a tissue or an organ, or a part thereof, a coating, a scaffold, or a controlled release dosage form.

(xvi) Use of gelatin according to any one of (i) to (v) or a hydrogel according to (vi) as a bio-ink or bio-resin.

BRIEF DESCRIPTION OF THE FIGURES

The teaching of the application is illustrated by the following FIGURES which are to be considered as illustrative only and do not in any way limit the scope of the claims.

FIG. 1: Effect of contaminating MAA in the gelMA on storage modulus (G') of gelMA-based hydrogels. Final G' (Pa, average 10 last min) at 20° C. of hydrogels based on gelMA solution with 0, 100, 300 or 600 ppm free MAA doping.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this encompasses also embodiments which consist essentially of the recited elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

The present application generally relates to functionalized gelatin for cross-linking gelatin to prepare e.g. gelatin-based hydrogels and films. More particularly, the application relates to methacryloyl-gelatin and acryloyl-gelatin.

Gelatin is a mixture of water-soluble proteins derived from collagen. Gelatin is obtained e.g. by partial hydrolysis of collagen, obtained by aqueous extraction of skin, tendons, ligaments, bones etc., from e.g. bovine, porcine, poultry or fish, in acid or alkali conditions, or by enzymatic hydrolysis, as known in the art. Gelatin obtained by acid treatment is called "type A gelatin", whereas "type B gelatin" is derived from alkali based process. Due to a more extensive deamination of asparagine and glutamine in type B gelatin, the isoelectric points (IEP) of type A gelatin and type B gelatin are at pH 7.0-9.0 and pH 4.9-5.1, respectively, which enables them to be positively and negatively charged at neutral physiological pH. In preferred embodiments, the invention relates to type A gelatin.

Gelatin does not constitute a uniform protein molecule, but comprises a variable amount of protein molecules of variable length. Preferably, the gelatin used herein has an average molecular weight within the range of 1500 Da to 300 kDa, preferably between 2000 Da and 300 kDa, between 4000 Da and 300 kDa, between 5000 Da and 300 kDa, between 10 kDa and 300 kDa, or between 20 kDa and 300 kDa, more preferably between 50 kDa and 300 kDa, most preferably between 100 kDa and 300 kDa, such as between 100 kDa and 275 kDa or between 100 kDa and 250 kDa. The molecular weight distribution of gelatin is usually measured by size exclusion high performance liquid chromatography (HPLC) techniques, and eluted fractions are detected by UV adsorption and the measured data are evaluated by suitable software, all techniques, known in the art, see e.g. Olijve et. al. (2000. Journal of Colloid and Interface Science 243: 476-482).

As used herein, the term "gelatin" also encompasses "gelatin derivatives", including chemically modified gelatin. The expression "gelatin modified with a chemical group or moiety (e.g. a methacryloyl group or an acryloyl group, an acetyl group or moiety, a phenol group or moiety, etc.)" as used herein denotes gelatin comprising said chemical group or moiety (e.g. a methacryloyl group or an acryloyl group, an acetyl group or moiety, a phenol group or moiety, etc.) e.g. attached to at least one amine group, at least one hydroxyl group, at least one carboxyl group and/or at least one phenol group of the gelatin.

As used herein "gelatin modified with a methacryloyl group", also referred to herein as "methacryloyl-modified gelatin", "methacryloyl-substituted gelatin" or "methacryloyl-gelatin" or 'gelatin methacryloyl" or 'gelMA" is defined as gelatin having free amines and/or free hydroxyls that have been substituted with at least one methacrylamide group and/or at least one methacrylate group. As used herein "gelatin modified with an acryloyl group", also referred to herein as "acryloyl-modified gelatin", "acryloyl-substituted gelatin" or "acryloyl-gelatin" or 'gelatin macryloyl" is defined as gelatin having free amines and/or free hydroxyls that have been substituted with at least one acrylamide group and/or at least one acrylate group. Gelatin comprises amino acids, some of which have side chains that terminate in amines (e.g., lysine, arginine, asparagine, glutamine) or hydroxyls (e.g., serine, threonine, aspartic acid, glutamic acid, tyrosine, hydroxyproline). One or more of these terminal amines and/or hydroxyls can be substituted with (meth)acryloyl groups to produce (meth)acryloyl-gelatin comprising (meth)acrylamide and/or (meth)acrylate groups, respectively.

The "degree of functionalization (DoF)" of gelatin generally refers to the percentage of functionalized primary amine groups and/or hydroxyl groups over total primary amine groups and/or hydroxyl groups. As used herein, the "degree of (meth)acrylamide substitution" refers to the percentage of free amine groups in the gelatin that have been substituted with a (meth)acrylamide group. As used herein, the "degree of (meth)acrylate substitution" refers to the percentage of free hydroxyl groups in the gelatin that have been substituted with a (meth)acrylate group. The degree of functionalization such as the degree of (meth)acrylamide substitution and/or the degree of (meth)acrylate substitution of gelatin can be determined by methods known per se. For example, the Fe(III)-acetohydroxamic acid method can be used for determining (meth)acrylation at hydroxyl groups. The Habeeb method (trinitrobenzenesulfonic acid (TNBS)-based spectrophotometric determination of (meth)acrylamide; Habeeb 1996. Anal. Biochem. 14:328-336), $^1$H-NMR and the fluoraldehyde assay (also known as o-Phthaldialdehyde (OPA)-based fluorometric determination of (meth)acrylamide) can be used for determining (meth)acrylation at amine groups. One can also use a combination of the aforementioned methods, such as a combination of a fluoraldehyde assay for quantifying amine group conversion and a Fe(III)-acetohydroxamic acid method for quantification of (meth)acrylate groups, which allows to determine the ratio of (meth)acrylate to (meth)acrylamide groups. In embodiments, the fluoraldehyde assay is used for determining the degree of (meth)acrylamide substitution.

In the (meth)acryloyl-gelatin disclosed herein, (meth)acryloylation is preferably at the free amine groups. In embodiments, the methacryloyl-gelatin has a degree of methacrylamide substitution of between 20% and 100%, preferably between 50% and 100%, more preferably between 80% and 100% such as between 85% and 100%, between 90% and 100 or between 95% and 100%. In embodiments, the methacryloyl-gelatin has a degree of methacrylate substitution of less than 20%, preferably less than 10%, 9%, 8%, 7% or 6%, more preferably less than 5%, 4%, 3%, 2% or 1%. In embodiments, the methacryloyl-gelatin has a degree of methacrylamide substitution of between 20% and 100% and a degree of methacrylate substitution of less than 20%, preferably a degree of methacrylamide substitution of between 20% and 100% and a degree of methacrylate substitution of less than 10%, more preferably a degree of methacrylamide substitution of between 50% and 100% and a degree of methacrylate substitution of less than 10%, even more preferably a degree of methacrylamide substitution of between 80% and 100% and a degree of methacrylate substitution of less than 10%.

In embodiments, the methacryloyl-gelatin comprises methacrylamide substitution and methacrylate substitution, and the ratio of methacrylamide substitution to methacrylate substitution is between 80:20 and 99:1, preferably between 90:10 and 99:1, more preferably between 95:5 and 99:1.

In embodiments, the acryloyl-gelatin has a degree of acrylamide substitution of between 20% and 100%, preferably between 50% and 100%, more preferably between 80% and 100% such as between 85% and 100%, between 90% and 100 or between 95% and 100%. In embodiments, the acryloyl-gelatin has a degree of acrylate substitution of less than 20%, preferably less than 10%, 9%, 8%, 7% or 6%, more preferably less than 5%, 4%, 3%, 2% or 1%. In embodiments, the acryloyl-gelatin has a degree of acrylamide substitution of between 20% and 100% and a degree of acrylate substitution of less than 20%, preferably a degree of acrylamide substitution of between 20% and 100% and a degree of acrylate substitution of less than 10%, more preferably a degree of acrylamide substitution of between 50% and 100% and a degree of acrylate substitution of less than 10%, even more preferably a degree of acrylamide substitution of between 80% and 100% and a degree of acrylate substitution of less than 10%.

In embodiments, the acryloyl-gelatin comprises acrylamide substitution and acrylate substitution, and the ratio of acrylamide substitution to acrylate substitution is between 80:20 and 99:1, preferably between 90:10 and 99:1, more preferably between 95:5 and 99:1.

The (meth)acryloyl-gelatin disclosed herein may be further modified and/or functionalized. In embodiments, the (meth)acryloyl-gelatin is further modified with an acetyl group or moiety, a phenol group or moiety, a thiol group or moiety, a norbornene group or moiety, a tetrazine group or moiety, an azide group or moiety, a furan group or moiety, a galactosyl group or moiety, or any combination thereof, preferably an acetyl group. Double chemically functionalized gelatin (meth)acryloyl acetyl may be produced as described in Hoch et al. (2012. Chemical tailoring of gelatin to adjust its chemical and physical properties for functional bioprinting. J. Mater. Chem. B 1:5675).

The gelMA and acryloyl-gelatin disclosed herein have low pyrogenic activity. Pyrogenic activity can be measured using a Monocyte Activation Test (MAT) assay as known in the art. The MAT assay allows to quantify both endotoxin and non-endotoxin pyrogen levels, but does not discriminate between the type of PAMP contamination. A cell-based pyrogen detection assay (PAMP assay) was developed by Fraunhofer Institute for Interfacial Engineering and Biotechnology IGB for detection and quantification different PAMPs, also non-endotoxins. This cell-based test system detects PAMPs using human Toll-like receptors (TLRs) (Burger-Kentischer et al. (2010) A new cell-based innate immune receptor assay for the examination of receptor activity, ligand specificity, signaling pathways and the detection of pyrogens. J Immunol Methods, 358: 93-103). More particularly, cells, e.g. NIH3T3 cells, express different TLR combinations allowing for the detection of different PAMPs. For example, cell lines with the receptor combination TLR1/2, TLR2/6, TLR4/CD14, TLR5, TLR7 and TLR9 allow for the detection of pyrogens from Gram+ bacteria (TLR1/2, TLR2/6), pyrogens from flagellated bacteria (TLR5), single-stranded viral RNA (TLR7), the cell line TLR4/CD14 allows for the detection of endotoxin from Gram– bacteria and the TLR9 cell line detects bacterial DNA rich in unmethylated CpG motifs. In embodiments, the gelMA and acryloyl-gelatin disclosed herein have a low content of pyrogens from Gram+ bacteria, pyrogens from flagellated bacteria, single-stranded viral RNA, endotoxin from Gram– bacteria and bacterial DNA rich in unmethylated CpG motifs.

In particular embodiments, the gelMA and acryloyl-gelatin have a low content of pyrogens from Gram+ bacteria and from flagellated bacteria, more particularly a low content of pyrogens from Gram+ bacteria.

In particular embodiments, the gelMA and acryloyl-gelatin disclosed herein are characterized by a low endotoxin or lipopolysaccharide (LPS) content, in particular an LPS content of less than 100 EU/g, more preferably less than 50 EU/g, even more preferably less than 20 EU/g, even more preferably less than 10 EU/g, even more preferably less than 5 EU/g, even more preferably less than 2 EU/g, most preferably less than 1 EU/g. In further particular embodiments, the gelMA and acryloyl-gelatin disclosed herein is (derived from) a type A gelatin and is characterized by an LPS content of less than 100 EU/g, more preferably less than 50 EU/g, even more preferably less than 20 EU/g, even more preferably less than 10 EU/g, even more preferably less than 5 EU/g, even more preferably less than 2 EU/g, most preferably less than 1 EU/g. In other further particular embodiments, the gelMA and acryloyl-gelatin disclosed herein is (derived from) a type B gelatin and is characterized by an LPS content of less than less than 20 EU/g, preferably less than 10 EU/g, more preferably less than 5 EU/g, even more preferably less than 2 EU/g, most preferably less than 1 EU/g. The term EU is known in the art and reflects 'endotoxin units'. One EU is approximately equivalent to 100 pg of *E. coli* lipopolysaccharide, the amount present in about $10^4$-$10^5$ bacteria. Herein, the term EU/g reflects the EU count per dry weight of gelatin/gelMA. The *Limulus* assay (LAL) is a well-known bioassay in the art to measure up to sub-picogram quantities of LPS. *Limulus* amebocyte lysate (LAL) is an aqueous extract of blood cells (amoebocytes) from the horseshoe crab, *Limulus polyphemus*. LAL reacts with bacterial endotoxin or lipopolysaccharide. This reaction is the basis of the LAL test, which is then used for the detection and quantification of bacterial endotoxins. For instance, a suitable LAL method to quantify the LPS levels is the chromogenic Endosafe method, e.g. from Charles River USA. Other accepted and recommended methods are the EndoZyme recombinant factor C method from Hyglos GmbH (Germany). Both said methods result in similar or identical measurement values and can therefore be used interchangeably.

Also advantageously, the gelMA and acryloyl-gelatin disclosed herein are substantially free of reagents and reaction products. In embodiments, the methacryloyl-gelatin disclosed herein comprises less than 150 ppm MAA or less than 100 ppm MAA or less than 50 ppm MAA, preferably less than 30 ppm MAA, more preferably less than 25 ppm MAA, even more preferably less than 20 ppm MAA. In embodiments, the methacryloyl-gelatin disclosed herein comprises less than 150 ppm MAA such as less than 140 ppm MAA, less than 130 ppm MAA, less than 120 ppm MAA or less than 110 ppm MAA, preferably less than 100 ppm MAA such as less than 90 ppm MAA, less than 80 ppm MAA, less than 70 ppm or less than 60 ppm, wherein the MAA content is determined on a sample of the methacryloyl-gelatin dissolved in 50 mM phosphate buffer, pH 9.5. In embodiments, the methacryloyl-gelatin disclosed herein comprises less than 100 ppm MAA or less than 50 ppm MAA, preferably less than 30 ppm MAA, more preferably less than 25 ppm MAA, even more preferably less than 20 ppm MAA, wherein the MAA content is determined on a sample of the methacryloyl-gelatin dissolved in water. In embodiments, the acryloyl-gelatin disclosed herein comprises less than 100 ppm acrylic acid or less than 50 ppm acrylic acid, preferably less than 30 ppm acrylic acid, more preferably less than 25 ppm acrylic acid, even more preferably less than 20 ppm acrylic acid. MAA can be measured as detailed in the Examples, in particular by dissolving a sample of the gelMA or the acryloyl-gelatin in water or in 50 mM phosphate buffer, pH 9.5, ultrafiltration of the dissolved sample (e.g. using 10-kDa Amicon Ultra Centrifugal Filters) and HPLC analysis of the filtrate. As shown by the present inventors, residues of methacrylic acid in the gelMA may interfere with the crosslinking of gelMA molecules. Due to its low methacrylic acid content, the gelMA disclosed herein is thus particularly suitable for crosslinking to form a hydrogel or a film.

Accordingly, a further aspect relates to a hydrogel comprising crosslinked gelMA or crosslinked acryloyl-gelatin as disclosed herein. Further disclosed herein are products derived from said hydrogels, such as films, bioadhesives, etc.

The term "hydrogel" as used herein refers to a network of hydrophilic polymer chains, such as crosslinked gelMA or crosslinked acryloyl-gelatin, forming a gel. The term "gel" denotes a substantially dilute crosslinked system which exhibits no flow when in the steady-state.

Processes for crosslinking gelMA and acryloyl-gelatin are well-known in the art. Typically, upon exposure to light in the presence of a photoinitiator, the (meth)acryloyl groups on one gelatin molecule can react with the (meth)acryloyl groups on another gelatin molecule to crosslink the (meth)acryloyl gelatin.

The term "photoinitiator" as used herein refers to any chemical compound, or a mixture of compounds, that decomposes into free radicals when exposed to light, e.g. ultraviolet light (UV) or visible light (VIS). Non-limiting examples of ultraviolet photoinitiators include 1-[4-(2-hydroxyethoxy)-phenyl]-2-hydroxy-2-methyl-1-propane-1-one (also known under the trade name Irgacure® 2959) and lithium phenyl-2,4,6-tri-methylbenzoylphosphinate (LAP). Visible light photoinitiators produce free radicals when exposed to visible light. Exemplary ranges of visible light useful for exciting a visible light photoinitiator include green, blue, indigo, and violet. Preferably, the visible light has a wavelength in the range of 450-550 nm. Non-limiting examples of visible light photoinitiators include, Eosin Y, riboflavin/triethanolamine, vinyl caprolactam, dl-2,3-diketo-1,7,7-trimethylnorcamphane (CQ), 1-phenyl-1,2-propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino)benzophenone, 4,4'-bis(diethylamino)benzophenone, 2-chlorothioxanthen-9-one, 4-(dimethylamino)benzophenone, phenanthrenequinone, ferrocene, dipheny 1(2,4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane (Ivocerin®), derivatives thereof, and any combination thereof.

The light irradiation time may be any suitable time for enabling crosslinking of the polymer. For example, the irradiation time may range from 10 seconds to 20 minutes, preferably from 1 minute to 20 minutes, more preferably from 2-15 minutes (for example 2, 3, 4, 5, 6, 7, 8, 9, 10, 11, 12, 13, 14 or 15 minutes).

The mechanical properties of a gelatin-based hydrogel can be tuned for various applications e.g. by the molecular weight of the gelatin used, by changing the degree of (meth)acryloyl substitution, gelMA or acryloyl-gelatin concentration, amount of photoinitiators, and light exposure time.

As used herein, the concentration of (meth)acryloyl-substituted gelatin is defined as the weight of (meth)acryloyl-substituted gelatin divided by the volume of solvent (w/v), expressed as a percentage. The solvent may be a pharmaceutically acceptable carrier. In embodiments of the hydrogel, the methacryloyl-substituted gelatin or the acryloyl-substituted gelatin is present at a concentration between 5% and 25% (w/v), between 17% and 25% (w/v), between 17% and 23% (w/v), or about 20% (w/v). In some embodiments, the methacryloyl-substituted gelatin or the acryloyl-substituted gelatin is present at a concentration between 5% and 15% (w/v), between 8% and 12% (w/v), or about 10% (w/v). In some embodiments, the methacryloyl-substituted gelatin or the acryloyl-substituted gelatin is present at a concentration between 10% and 40% (w/v), 15% and 35% (w/v), 20% and 30% (w/v), or about 5%, 10%, 15%, 20%, or 25% (w/v).

The chemically modified gelatin, in particular the methacryloyl-gelatin and acryloyl-gelatin, and the hydrogel according to the invention may be used for a variety of applications including, but not limited to, the manufacture or repair of tissue (e.g. cartilage, soft tissue) in a human or non-human animal, and the use as a bio-ink or bio-resin for the 3-dimensional biofabrication or 3-dimensional bioprinting of a biological construct. The biological construct may be any animal tissue or organ, or part thereof, that is able to be manufactured using a biofabrication or bioprinting technique, e.g. a scaffold containing cells which may be porous or non-porous.

The term "bio-ink" refers to a hydrogel that can be 3D-printed, 3D-plotted or fabricated into a particular shape or construct, and which is cytocompatible. The hydrogel may or may not incorporate living cells and/or growth factors, etc.

The term "bio-resin" denotes a hydrogel that can be 3D-printed or fabricated into a particular shape or construct using laser or light projection-based light stereolithography, or similar lithographic techniques, and which is cytocompatible. The hydrogel may or may not incorporate living cells, drugs and/or growth factors, etc.

Accordingly, an aspect relates to a gelMA or an acryloyl-gelatin disclosed herein or a hydrogel comprising the gelMA or the acryloyl-gelatin disclosed herein for use in medicine. A further aspect relates to a gelMA or an acryloyl-gelatin disclosed herein or a hydrogel comprising the gelMA or the acryloyl-gelatin disclosed herein for use in repairing a tissue or an organ, or a part thereof, in a human or non-human animal. In embodiments, the tissue or organ is selected from bone tissue, cartilage and vascular tissue. In embodiments, a gelMA or an acryloyl-gelatin disclosed herein or a hydrogel comprising the gelMA or the acryloyl-gelatin disclosed herein is provided herein for use as bioadhesive or bioglue. The gelMA or the acryloyl-gelatin or the hydrogel comprising the gelMA or the acryloyl-gelatin disclosed herein may be used, for example, for orthopedic applications, for orthodontic applications, or for cosmetic and plastic surgery.

A related aspect is directed to in vitro or ex vivo use of a gelMA or an acryloyl-gelatin disclosed herein or a hydrogel comprising the gelMA or the acryloyl-gelatin disclosed herein for manufacturing a tissue or an organ, or a part thereof. In embodiments, the tissue or organ is selected from bone tissue, cartilage and vascular tissue. Also disclosed herein is a tissue-engineered tissue or organ, or part thereof, comprising a gelMA or an acryloyl-gelatin disclosed herein or a hydrogel comprising the gelMA or the acryloyl-gelatin disclosed herein.

Another aspect is directed to in vitro or ex vivo use of a gelMA or an acryloyl-gelatin disclosed herein or a hydrogel comprising the gelMA or the acryloyl-gelatin disclosed herein for the manufacture of a controlled release dosage form or a biological construct. The biological construct can be, for example, a coating on a (solid) support suitable for adhesion and proliferation of cells, or a scaffold suitable for containing cells, or drugs and/or vectors.

Yet a further aspect relates to uses of a gelMA or an acryloyl-gelatin disclosed herein or a hydrogel comprising the gelMA or the acryloyl-gelatin disclosed herein as a bio-ink or bio-resin. In further embodiments, the bio-ink or bio-resin is used for 3-dimensional biofabrication or 3-dimensional bioprinting of a biological construct. The biological construct may be an animal tissue or organ, or part thereof. The biological construct can also be a scaffold suitable for containing cells, or a scaffold suitable for containing e.g. drugs and/or vectors (e.g. for drug delivery/gene therapy applications). The biological construct can also be a bioresorbable screw or other biomaterial (e.g. bioadhesive). In embodiments, the biological construct is a scaffold suitable for containing cells. In embodiments, the biological construct is a coating. Also disclosed herein, is a biological construct comprising the gelMA or the acryloyl-gelatin disclosed herein or a hydrogel comprising the gelMA or the acryloyl-gelatin disclosed herein.

Yet a further aspect relates to a method for preparing a methacryloyl-gelatin and an acryloyl-gelatin as disclosed herein. The present inventors have surprisingly found that purification of an aqueous reaction medium of gelMA or acryloyl-gelatin according to the method described in WO 2016/085345, not only removes lipopolysaccharides from the medium, but also other pyrogens as well as the methacrylic acid and acrylic acid that are formed during respectively, the methacryloylation reaction and acryloylation reaction. As such, no dialysis of the reaction medium is required, resulting in a faster process that provides gelMA that has a low LPS content, a low pyrogen content and a low methacrylic acid or acrylic acid content as specified elsewhere herein.

Accordingly, in a further aspect, the invention relates to a method of preparing a (meth)acryloyl-gelatin as disclosed herein, said method comprising the following steps:
a) modifying gelatin with a (meth)acryloyl group by reacting gelatin with (meth)acryl anhydride;
b) lowering the pH of the reaction medium to a value between 2.0 and 5.0, preferably between 2.0 and 4.0, more preferably between 3.0 and 4.0 or between 2.0 and 3.5, even more preferably between 3.0 and 3.5;
c) adding a micelle-forming surfactant to the reaction medium;
d) contacting the medium of step c) with a solid adsorbent;
e) separating the solid adsorbent of step d) from the medium;
f) recovering the medium comprising the methacryloyl-gelatin; and
g) optionally drying the medium comprising the (meth)acryloyl-gelatin of step f).

An alternative method of preparing a (meth)acryloyl-gelatin as disclosed herein comprises the following steps:
a) modifying gelatin with a (meth)acryloyl group by reacting gelatin with (meth)acryl anhydride;
$b_1$) lowering the pH of the reaction medium to a value between 4.0 and 9.0, preferably between 4.0 and 6.0, more preferably between 4.0 and 6.0, even more preferably between 4.5 and 5.5;
c) adding a micelle-forming surfactant to the reaction medium;
$b_2$) lowering the pH of the medium of step c) to a value between 2.0 and 4.0, preferably between 3.0 and 4.0 or between 2.0 and 3.5, more preferably between 3.0 and 3.5;
d) contacting the medium of step $b_2$) with a solid adsorbent;
e) separating the solid adsorbent of step d) from the medium;
f) recovering the medium comprising the methacryloyl-gelatin; and
g) optionally drying the medium comprising the (meth)acryloyl-gelatin of step f).

Any type of gelatin, e.g. type A or type B gelatin, of e.g. bovine, porcine, poultry or fish origin, can be used in the methods described herein. In embodiments, type A gelatin is used. In other embodiments, type B gelatin is used.

Methacryloylation and acryloylation of gelatin can be performed by reacting gelatin with respectively, methacrylic anhydride and acrylic anhydride in a suitable buffer, e.g. in carbonate buffer at pH 9.0 or in phosphate-buffered saline (PBS), at a temperature of 50° C. for 60-180 min such as 60 minutes or 120-180 minutes. The degree of (meth)acryloylation of the gelMA can be tailored by varying the (meth)acrylic anhydride:gelatin ratio as described in Shirahama et al. (2016). During the reaction, gelMA and acryloyl-gelatin are formed, respectively as well as methacrylic acid or acrylic acid.

The pH of the reaction medium may be lowered before adding the micelle-forming surfactant to a value between 2.0 and 5.0, preferably between 2.0 and 4.0, more preferably between 3.0 and 4.0 such as a value of about 3.5 or between 2.0 and 3.5 such as a value of about 3.0, even more preferably between 3.0 and 3.5 (step b) in the methods described herein). Alternatively, the pH of the reaction medium may be lowered to a value between 4.0 and 9.0, preferably between 4.0 and 6.0, more preferably between 4.0 and 6.0, even more preferably between 4.5 and 5.5 before adding the micelle-forming surfactant (step $b_1$) in the methods described herein), and may be further lowered to a value between 2.0 and 4.0, more preferably between 3.0 and 4.0 such as a value of about 3.5 or between 2.0 and 3.5 such as a value of about 3.0, even more preferably between 3.0 and 3.5, after adding the micelle-forming surfactant and before contacting the medium with the solid adsorbent (step $b_2$) in the methods described herein). Advantageously, when performing the next method steps at low pH, LPS, pyrogens and methacrylic acid or acrylic acid are removed more efficiently.

In the methods described herein, a micelle-forming surfactant is added to the reaction medium. A micelle-forming surfactant is capable of forming micelles (soluble aggregates) in solution. Micelle-forming surfactants are known in the art, and are e.g. described in WO 2009/15440. The micelle-forming surfactant can be an ionic surfactant, such as a cationic or anionic surfactant. Preferably, the surfactant is non-ionic surfactant as such a surfactant tends to form micelles at lower concentration as compared to ionic surfactants. Further, ionic surfactants may interact with the gelatin by ionic bonds, and are more difficult to remove. Preferably, the micelle-forming non-ionic surfactant is an ethoxylated surfactant, preferably an alkylphenol ethoxylate, the alkylphenol ethoxylate preferably being represented by the formula $C_xH_{2x-1}$—$C_6H_4$—O—$(C_2H_4O)_nH$, wherein x is 4-12 and n is 7.5-14, X preferably being 8 and n preferably being 8-13, more preferably 8.5-12.5, most preferably 9-12, in particular Triton X-100, Triton X-102, or mixtures thereof. The Triton X-series of nonionic surfactants are prepared by the reaction of octylphenol with ethylene oxide. The products are of the type commonly described as alkylaryl polyether alcohols and have the following structural formula: $C_8H_{17}$ $C_6H_5(CH_2CH_2O)_{9.7}$ (Triton X-100) and $C_9H_{19}$ $C_6H_5(CH_2CH_2O)_{12.3}$ (Triton X-102). Other non-ionic surfactants that are suitable comprise nonylphenoxypolyethoxyethanols $C_{15}H_{24}O(C_2H_4O)_n$, n being 3-40, such as nonoxynol-4, nonoxynol-15 and nonoxynol-30, or polyethylene glycol sorbitan monoesters of C12-C18 fatty acids, such as TWEEN. CHAPSO (3-([3-cholamidopropyl]dimethyl ammonio)-2-hydroxyl-1-propanesulfonate is another suitable non-ionic surfactant.

As described in WO 2009/15440, as a result of adding a micelle-forming surfactant, LPS is monomerised and said monomers are believed to interact with the surfactant, forming micelle complexes comprising surfactant and LPS.

In order to allow for efficient removal of the LPS, and preferably also of other pyrogens, in particular pyrogens from Gram+ bacteria and pyrogens from flagellated bacteria, more particularly pyrogens from Gram+ bacteria, the weight ratio of gelatin, in particular gelMA or acryloyl-gelatin, to added surfactant, in particular non-ionic surfactant, is preferably 2000:1 or less, more preferably 500:1 or less, even more preferably 250:1 or less, most preferably 50:1 or less. Indeed, at higher weight ratios, i.e. where there is relatively more gelatin, not all LPS will be bound by the surfactant. Preferably, the surfactant is added to the reaction medium at a concentration of 0.01-1.5 w/w %, preferably 0.015-1.0 w/w %, more preferably 0.020-0.50 w/w %.

In step d) of the methods described herein, the medium of step c) or the medium of step $b_2$), which may contain soluble aggregates comprising surfactant, LPS and monomers thereof and/or other pyrogens, in particular pyrogens from Gram+ bacteria and pyrogens from flagellated bacteria, more particularly pyrogens from Gram+ bacteria, is contacted with a solid adsorbant. In addition to binding the surfactant, and preferably also LPS, the adsorbent also preferably binds other pyrogens, in particular pyrogens from Gram+ bacteria, pyrogens from flagellated bacteria, single-stranded viral RNA, and bacterial DNA rich in unmethylated CpG motifs, and methacrylic acid or acrylic acid.

The solid adsorbent can be any suitable adsorbent, capable of binding the surfactant, and preferably also LPS, other pyrogens and (meth)acrylic acid, known to the skilled person, such as a hydrophobic adsorbent. The adsorbent is preferably insoluble, and suitable adsorbents comprises clays, such as (activated) diatomaceous earth or clays, phyllosilicates, such as aluminium phyllosilicate, smectite minerals and hydrophobic adsorbents, such as activated carbon, for example Norit SX Plus or Norit ROX 0.8 (Cabot, the Netherlands), or 3M ZetaCarbon filter cartridges, e.g. such as of the type R55S or R30L3S (3M, USA). Also mixtures of one or more adsorbents can be applied. In preferred embodiments, the solid adsorbent is activated carbon. Contacting the medium with a solid adsorbent can be done e.g. by adding particulate adsorbent to the medium, or by passing the medium through a filter element comprising the said adsorbent or over a column stacked with the adsorbent, or by incubating the medium with a carrier having the adsorbent present on the outer surface thereof.

The solid adsorbent is preferably added to the medium in a weight ratio to the surfactant of at least 2.5:1, more preferably of at least 3.0:1, most preferably of at least 3.5:1. The solid adsorbent is preferably added to the medium in a concentration of 0.1-3 w/w %, preferably of 0.5-1 w/w %. In case filter elements or systems are used, it may be preferred to use similar amounts of adsorbent in the filter system.

The contacting step is performed for a sufficient time to allow proper adsorption of the surfactant, resulting in removal of the surfactant and the LPS and/or other pyrogens, in particular pyrogens from Gram+ bacteria and pyrogens from flagellated bacteria, more particularly pyrogens from Gram+ bacteria, which are bound to the surfactant, and preferably also to allow adsorption of the (meth)acrylic acid, LPS and other pyrogens, in particular pyrogens from Gram+ bacteria, pyrogens from flagellated bacteria, single-stranded viral RNA, and bacterial DNA rich in unmethylated CpG motifs, and methacrylic acid, which are bound to the adsorbent. Preferably, the adsorbent is contacted with the (aqueous) medium for 5 minutes to 1 hour, more preferably for 10-30 minutes.

In the next step (e)) of the methods described herein, the solid adsorbent is removed from the medium. The skilled person is aware of suitable ways to bring an aqueous medium in contact with a solid adsorbent and to separate the adsorbent from the medium. The said separation can e.g. comprise centrifugation or filtration in case the adsorbent is added as a particulate to the medium, where filtration is preferred in view of industrial applicability. For example, the solid adsorbent can be added to the medium (of step c) or step $b_2$) and, after allowing the surfactant and preferably also the LPS, other pyrogens and MAA or acrylic acid to bind to the adsorbent, the adsorbent can be removed e.g. by filtration, sedimentation or centrifugation and the like. In another example, the solid adsorbent can be present in a filter, and the medium (of step c) or step $b_2$) of the methods described herein) is passed through the said filter, or through a series of such filters, while the filters can optionally be washed in order to optimize the yield of the filtrate. This way, steps d), e) and f) of the herein described methods can be combined in a single filtration step.

Following the separation of the solid adsorbent, the medium comprising the methacryloyl-gelatin or the acryloyl-gelatin is recovered.

Preferably steps c)-f) of the methods described herein are performed at a temperature below the cloud point of the surfactant used. As used herein, the term "cloud point" refers to the temperature at which the surfactant forms insoluble aggregates in the medium. Said temperature depends on the conditions of the medium, such as salt concentration. When no specific conditions are given, the cloud point is defined herein as the temperature where a 1 w/w % aqueous solution forms insoluble aggregates. So, if the temperature is described to be below the cloud point of a surfactant, said temperature is 68-69° C. (i.e. for a 1 w/w % Triton X-100 solution), but in case of a 16-25 w/w % NaCl solution, said cloud point is room temperature. The cloud point can conveniently be determined under the given circumstances, by determining the light absorbance of the solution at 620 nm without addition of the surfactant, and check whether the absorbance increases when the envisaged amount of surfactant is added. Above the cloud point, the absorbance is increased.

In embodiments, steps c)-f) are performed at a temperature of 65° C. or less, more preferably of 62° C. or less, even more preferably of 60° C. or less. In embodiments, steps c)-f) are performed at a temperature between 30° C. and 65° C., preferably between 30° C. and 60° C., more preferably between 30° C. and 50° C. or between 30° C. and 40° C., even more preferably between 30° C. and 35° C.

In embodiments, the pH of the medium is between 2.0 and 5.0, preferably between 2.0 and 4.0, more preferably between 3.0 and 4.0 such as at about 3.5 or between 2.0 and 3.5 such as at about 3.0, even more preferably between 3.0 and 3.5 throughout the method steps c)-f). At such pH, the temperature is preferably below 35° C., more preferably between 30° C. and 35° C., such as at about 30° C.

In other embodiments, the pH of the medium is between 2.0 and 5.0, preferably between 2.0 and 4.0, more preferably between 3.0 and 4.0 such as at about 3.5 or between 2.0 and 3.5 such as at about 3.0, even more preferably between 3.0 and 3.5 throughout the method steps d)-f). At such pH, the temperature is preferably below 35° C., more preferably between 30° C. and 35° C., such as at about 30° C.

Following the recovery of the medium comprising the methacryloyl-gelatin or the acryloyl-gelatin, the methods may further comprise a step of increasing the pH of the medium to between 3.5 and 9.0, preferably between 4.0 and 8.0, more preferably between 5.0 and 7.0. As noted before, the methods described herein results in methacryloyl-gelatin or acryloyl-gelatin with low LPS content, in particular an LPS content of less than 100 EU/g, more preferably less than 50 EU/g, even more preferably less than 20 EU/g, even more preferably less than 10 EU/g, even more preferably less than 5 EU/g, even more preferably less than 2 EU/g, most preferably less than 1 EU/g. In particular, the gelMA or acryloyl-gelatin comprises at least 50 times less LPS, preferably at least 100 times, more preferably at least 150 times, even more preferably at least 200 times and most preferably at least 250 times less LPS as compared to the LPS content of the gelatin used as starting material of step a). The LPS count can be determined on the recovered medium using e.g. the LAL assay as described elsewhere herein.

The obtained methacryloyl-gelatin or acryloyl-gelatin is further characterized by a low content of non-endotoxin pyrogens, in particular a low content of pyrogens from Gram+ bacteria, pyrogens from flagellated bacteria, single-stranded viral RNA, endotoxin from Gram−bacteria and bacterial DNA rich in unmethylated CpG motifs, more particularly a low content of pyrogens from Gram+ bacteria and from flagellated bacteria, even more particularly a low content of pyrogens from Gram+bacteria. In particular, the gelMA or acryloyl-gelatin comprises at least 10 times less pyrogens from Gram+ bacteria, preferably at least 20 times less, more preferably at least 50 times, even more preferably at least 100 times, at least 150 times, at least 200 times or at least 250 times less, as compared to the content of pyrogens from Gram+ bacteria of the gelatin used as starting material of step a). In particular, the gelMA or acryloyl-gelatin comprises at least 10 times less pyrogens from flagellated bacteria, preferably at least 20 times less, more preferably at least 50 times, even more preferably at least 100 times, at least 150 times, at least 200 times or at least 250 times less, as compared to the content of pyrogens from flagellated bacteria of the gelatin used as starting material of step a). In particular, the gelMA or acryloyl-gelatin comprises at least 10 times less bacterial DNA rich in unmethylated CpG motifs, preferably at least 20 times less, more preferably at least 50 times, even more preferably at least 100 times, at least 150 times, at least 200 times or at least 250 times less, as compared to the content of less bacterial DNA rich in unmethylated CpG motifs of the gelatin used as starting material of step a). less single-stranded viral RNA.

Further, the methods described herein result in methacryloyl-gelatin with low methacrylic acid content, in particular less than 100 ppm, preferably less than 50 ppm, more preferably less than 30 ppm of methacrylic acid, preferably as determined on a sample of the methacryloyl-gelatin dissolved in water, or less than 150 ppm, preferably less than 100 ppm of methacrylic acid as determined on a sample of the methacryloyl-gelatin dissolved in 50 mM phosphate buffer, pH 9.5, or acryloyl-gelatin with low acrylic acid content, in particular less than 30 ppm of acrylic acid. Thus, the present methods provide a purified gelMA or acryloyl-gelatin in a single round of the (6 or 7) steps a)-f) described above.

As the methods described herein result in (meth)acryloyl-gelatin with low (meth)acrylic acid content without the need of a dialysis step, the methods are preferably free of a dialysis step. Such dialysis step is in general time-consuming, and therefore, the present methods are more efficient, especially for large scale production of a purified gelMA and acryloyl-gelatin.

In embodiments, the methods further comprise a step of drying the recovered medium comprising the gelMA or acryloyl-gelatin, optionally after having increased the pH of the medium, e. g. by freeze-drying to a white porous foam (Van Den Bulcke et al. 2000. Structural and rheological properties of methacrylamide modified gelatin hydrogels. Biomacromolecules 1:31-38).

The present invention will now be further illustrated by means of the following non-limiting examples.

EXAMPLES

Example 1: GelMA Preparation Method and Properties of the GelMA

Materials and Methods

Synthesis of GelMA 15-20% gelatin (pig skin, type A, Bloom 200) solution in 1.25 M carbonate buffer at pH 9.0 was reacted with methacrylic anhydride in a 1:1 ratio for 120-180 minutes at 50° C. During the reaction, methacrylic acid was formed. The pH of the reaction medium was lowered to pH 3.5 using HCl to remove the carbonate. 1.12% (on weight of gelatin) Triton-X100 was added to the medium and the medium was maintained under agitation during 1 hour. The medium was then filtered over a column packed with active carbon.

Determination of LPS Content

LPS content was determined using the EndoZyme II assay kit (Hyglos) according to the manufacturer's instructions. Briefly, gelMA solutions in ultrapure water were prepared at 2.50% (w/w) and 10×, 20×, 50×, 100×, etc. dilutions depending on the expected LPS content. 100 μL of each sample was added into a well of a multi-well plate and mixed with 100 μL of the assay reagent prepared according to the manufacturer's instructions. Fluorescence intensity of the resulting mixtures was monitored in a microplate fluorescence reader (BopTek; excitation/emission=380 nm/455 nm). A dilution series of an endotoxin standard (*E. coli* O55: B5) reconstituted in endotoxin free water at 50 EU/mL was used as calibration standard; and endotoxin fee water was used as blank.

Determination of MAA Content

8% (w/w) solutions of the gelMA samples in water or 50 mM phosphate buffer, pH 9.5 were made. The samples were allowed to swell for 15 min at room temperature, and were then put at 50° C. for 30 min until the samples were visually completely dissolved. 0.5 mL of the sample solutions were added to 10-kDa Amicon Ultra Centrifugal Filters (Milipore) and put at 50° C. (oven) for 10 min, after which they were centrifuged at 12000×g for 30 min at 40° C. Afterwards, the filtrates were collected for HPLC analysis.

A dilution series of methatcrylic acid ranging from 0.1 ppm to 100 ppm was made by preparing a 1% (w/w) of methacrylic acid in water or 50 mM phosphate buffer, pH 9.5 and making 2-fold dilutions in water or 50 mM phosphate buffer, pH 9.5, and used as standard.

Determination of DNA Content

A stock concentration of 0.1 mg/mL salmon testes dsDNA standard was prepared in TE buffer (10 mM Tris-HCl with 1 mM EDTA in water, pH=8) and diluted further to a stock concentration of 10 µg/mL.

Quantification standards ranging from 10 µg/ml to 0 µg/ml in TE buffer. 10% (w/w) gelatin samples were prepared in TE buffer; the samples were allowed to swell for 30 min and dissolved at 40° C. using a water bath.

95 µl of a master mix containing 94 µL TE buffer and 1 µL SYBR Green (100×), and 5 µl of a sample or standard were added in the wells of a black well fluorescent 96-well plate and mixed by pipetting up and down. The 96-well plate was covered and incubated at 37° C. and 700 rpm for 30 min. Fluorescence was measured at Ex535 nm/Em617 nm using a Synergy™ Mx fluorometer (BioTek) at 25° C. according to the manufacturer's instructions.

Results

TABLE 1

Comparison of LPS content, MAA content and DNA content of gelMAs according to the invention (Rousselot 1-3) and gelMAs on the market.

| Sample | LPS (EU/g) | MAA (ppm) determined on gelMA dissolved in water | MAA (ppm) determined on gelMA dissolved in 50 mM phosphate buffer, pH 9.5 | DNA (ppm) |
|---|---|---|---|---|
| Rousselot1 | 5 | 5.45 | 16.5 | 2.33 |
| Rousselot2 | 2 | 8.92 | 23.8 | 3.87 |
| Rousselot3 | 5 | 6.37 | 34.2 | 3.22 |
| Sigma gelMA (900629, 40% sub, 300 bl) | 90000 | 43 | 145 | 17.45 |
| Sigma GelMA (900496, 80% sub, 300 bl) | 110 | 53 | 151 | 15.88 |
| Claro BGl800 | 75 | 569 | 739 | 3.96 |

The methacryloyl-gelatin according to the present invention is thus characterized by a low endotoxin content and a low MAA content e.g. compared to gelMAs on the market. They are further characterized by a low DNA content, which indicates that pyrogenic activity based on nucleic acids is low in the gelMAs of the invention.

Example 2: Cross-Linking

The impact of contaminating methacrylic acid on gelMA hydrogels rheological characteristics was tested.

Materials and Methods 65 g of gelMA (prepared according to Example 1) solution at 10% (w/v) and Irgacure (Irgacure 2959 photoinitiator (2-hydroxy-4'-(2-hydroxyethoxy)-2-methylpropiophenone)) at 0.5% (w/v) was prepared in phosphate buffered saline (PBS), pH 7.4 in 150 mL Falcon tubes wrapped in aluminum foil. First, 2×162.5 mg Irgarcure was dissolved in 2×29.1 ml PBS. The Irgacure powder was dispersed in PBS by pipetting the mix up and down several times, and the solutions were placed in a water bath at 60° C. during approximately 20 min. Then, 2×3.25 g gelMA was added, vortexed and reserved in the water bath at 60° C. The mixes were regularly vortexed until solubilization was complete. Both solutions were merged in one tube and vortexed.

The gelMA and Irgarcure solution was split in 8×7 mL in 15 mL Flacon tubes wrapped with aluminum foil, and 0 µl (none MAA), 0.7 µl (100 ppm MAA), 2.1 µl (300 ppm MAA) or 4.2 µl (600 ppm MAA) methacrylic acid (11.67 M) was added to the tubes in duplicate. The tubes were vortexed and reserved in a water bath at 40° C. for 90 minutes, after which they were taken out of the water batch and allowed to rest at room temperature overnight.

20 minute prior to analysis, the samples were remolten in a water bath at 40° C., and for each sample, 3×2 ml solution was transferred from the tube in 3 Elastosens™ sample holders, which had been calibrated on the machine. One drop surfactant was added in each sample holder and UV light (365 nm) was shined on the samples during 20 min at room temperature (UV lamp (UVMLS-38 EL Series 3UV-254/302/365 nm/8W, 0.16 A) set at 365 nm). Immediately after this UV curing, the sample holders were placed in the Elastosens™ Bio$^2$ instrument and rheology analysis was conducted at 20° C. during 45 min with measurements every 15 seconds.

Results

As shown in FIG. 1, the final storage modulus (G') decreases with increasing concentration of MAA, which indicates that elasticity of the gelMA-based hydrogel decreases when contaminating MAA is present in the gelMA.

Example 3: Comparison of GelMAs Prepared by a Method According to an Embodiment of the Invention and a Method Based on Dialysis Material and Methods Two types of gelatin: a type A 250 Bloom and a type B 250 bloom gelatin, were methacryloyl-modified according to the method described in Pahoff et al. (2019 J. Mater Chem. B 7:1761-1772) up to a degree of functionalization of 40%. The start gelatins obtained from a type A and B process, were contaminated with respectively, 1046 and 4782 endotoxin units (EU) per gram of gelatin (Hyglos endozyme). Methacrylic acid residues and LPS contamination were measured as described in Example 1 in ppm, and EU per gram of gelatin, respectively. The gelMA was dissolved in 50 mM phosphate buffer, pH 9.5 for determining MAA content.

In the comparative method, methacrylic acid by-product was removed from the gelMA solutions by dialysis against ultrapure water (MilliQ, Merck Millipore). Twenty milliliter aliquots of the gelMA solutions were transferred to 5 dialysis tubes (Dialysis tubing cellulose membrane, MWCO 14 kDa, cat. N°: D9527-100FT, Sigma-Aldrich) and each of these were submerged into 2.5 liter of water. Dialysis proceeded at 40° C., and the water was exchanged every 24 h. At days 1, 2, 3, 4, and 7, one tube was removed and its methacrylic acid and LPS content were measured as described in Example 1. The gelMA was dissolved in 50 mM phosphate buffer, pH 9.5 for determining MAA content.

In the method according to an embodiment of the invention, five 40 ml aliquots of the gelMA solutions were pH adjusted by adding diluted HCl to a pH of 2.0, 2.5, 3.0, 3.5, and 4.0 (all measured at 40° C.) and 0.1% (on gelatin content) of Triton-X100 was added to each aliquot. Each aliquot was then divided in two, with one of those serving as a negative control on the effect of the pH reduction, and Triton-X100 addition on the methacrylic acid content and the LPS contamination. Five gram of Norit active carbon powder (S268, active carbon Norit SX plus 8013-1) was added to each of the experimental tubes, and these tubes were incubated on rotary shaker for 1 h at 40° C. Next, these tubes were centrifuged at 2000 rpm for 30 minutes, and the supernatant was filtered (0.45 µm) and analyzed as described in Example 1 for its methacrylic acid and LPS content. The gelMA was dissolved in 50 mM phosphate buffer, pH 9.5 for determining MAA content.

Results

Table 2 shows the MAA content (ppm) and LPS content (EU/g) of purified gelMA obtained by a method based on dialysis or by a method according to an embodiment of the invention.

TABLE 2

Comparison of MAA content (ppm) and LPS content (EU/g) of purified gelMA obtained by a method based on dialysis or by a method according to an embodiment of the invention.

| dialysis-based method/type B gelatin | MAA (ppm) | LPS (EU/g) | method according to an embodiment of the invention/type B gelatin | MAA (ppm) | LPS (EU/g) |
|---|---|---|---|---|---|
| before dialysis | 50548 | 4782 | before purification | 50548 | 4782 |
| 24 h/1 day | 2831 | 4589 | pH 2.0 | 20.5 | 53 |
| 48 h/2 days | 579 | 5391 | pH 2.5 | 29.1 | 48 |
| 72 h/3 days | 308 | 5729 | pH 3.0 | 56.3 | 67 |
| 96 h/4 days | 272 | 5701 | pH 3.5 | 128 | 61 |
| 168 h/7 days | 187 | 6056 | pH 4.0 | 383 | 73 |

| dialysis-based method/type A gelatin | MAA (ppm) | LPS (EU/g) | method according to an embodiment of the invention/type A gelatin | MAA (ppm) | LPS (EU/g) |
|---|---|---|---|---|---|
| before dialysis | 51261 | 1046 | before purification | 51261 | 1046 |
| 24 h/1 day | 1785 | 928 | pH 2.0 | 19.3 | 1.1 |
| 48 h/2 days | 610 | 961 | pH 2.5 | 32.1 | 0.8 |
| 72 h/3 days | 299 | 1088 | pH 3.0 | 60.5 | 0.7 |
| 96 h/4 days | 256 | 1039 | pH 3.5 | 136 | 1.3 |
| 168 h/7 days | 155 | 1161 | pH 4.0 | 351 | 1 |

Example 4: GelMA Preparation Method

Material and Methods

GelMA was synthesized as described in Example 1 with the following modifications: the pH of the reaction medium was lowered to pH 5.5 before the addition of the Triton-X100, and after incubation for 1 hour under agitation, the pH of the medium was further lowered to pH 3.5 using HCl, after which the medium was filtered over a column packed with active carbon. Methacrylic acid residues and LPS contamination of the obtained gelMA were measured as described in Example 1 in ppm, and EU per gram of gelatin, respectively. The gelMA was dissolved in 50 mM phosphate buffer, pH 9.5 for determining MAA content.

Results

TABLE 3

LPS content and MAA content of gelMAs obtained by a method according to an embodiment of the invention.

| Sample | LPS (EU/g) | MAA (ppm) determined on gelMA dissolved in 50 mM phosphate buffer, pH 9.5 |
|---|---|---|
| Rousselot 4 | 4 | 28.9 |
| Rousselot 5 | 2 | 32.7 |

STATEMENTS

The present invention is in particular captured by any one or any combination of one or more of the below numbered aspects and embodiments with any other aspects, statement and/or embodiments:

Aspect 1: Gelatin modified with a methacryloyl group or an acryloyl group, having a lipopolysaccharide content of less than 100 EU/g, preferably less than 50 EU/g, more preferably less than 20 EU/g, even more preferably less than 10 EU/g, even more preferably less than 5 EU/g, even more preferably less than 2 EU/g, most preferably less than 1 EU/g.

Aspect 2: Gelatin according to aspect 1, comprising less than 30 ppm of methacrylic acid or acrylic acid.

Aspect 3: Gelatin according to aspect 1 or 2, having a low content of pyrogens from Gram+ bacteria, pyrogens from flagellated bacteria, single-stranded viral RNA and bacterial DNA rich in unmethylated CpG motifs, preferably a low content of pyrogens from Gram+ bacteria and from flagellated bacteria, more preferably a low content of pyrogens from Gram+bacteria.

Aspect 4: Gelatin according to any one of aspects 1 to 3, wherein said gelatin is type A gelatin.

Aspect 5: Gelatin according to any one of aspects 1 to 4, having a degree of methacrylamide substitution or acrylamide substitution of between 20% and 100%, preferably between 50% and 100%, more preferably between 80% and 100%, and a degree of methacrylate substitution of less than 10%.

Aspect 6: Gelatin according to any one of aspects 1 to 5, wherein said gelatin is further modified with an acetyl group.

Aspect 7: Hydrogel comprising a gelatin modified with a methacryloyl group or an acryloyl group according to any one of aspects 1 to 6, and a cross-linking agent.

Aspect 8: A film comprising a hydrogel according to aspext 7.

Aspect 9: Method for preparing gelatin modified with a methacryloyl group or acryloyl according to any one of aspects 1 to 6, comprising the steps of:
 a) modifying gelatin with a methacryloyl group or an acryloyl group by reacting gelatin with methacrylanhydride or acrylanhydride;
 b) lowering the pH of the reaction medium to a value between 3 and 4;

c) adding 0.01-1.5 w/w % of a micelle-forming surfactant to the acidic reaction medium;

d) contacting the medium of step c) with a solid adsorbent;

e) separating the solid adsorbent of step d) from the medium; and f) recovering the medium comprising the methacryloyl gelatin or the gelatin-acryloyl.

Aspect 10: The method according to aspect 9, wherein said micelle-forming surfactant comprises a non-ionic surfactant, preferably wherein the surfactant is Triton X-100 or Triton X-102, or mixtures thereof.

Aspect 11: The method according to aspect 9 or 10, wherein said solid adsorbent is a hydrophobic adsorbent, preferably activated carbon.

Aspect 12: The method according to any one of aspects 9 to 11, further comprising a step of drying the medium comprising the methacryloyl gelatin or the gelatin-acryloyl.

Aspect 13: Gelatin according to any one of aspects 1 to 6 or a hydrogel according to aspect 7 for use in medicine.

Aspect 14: In vitro or ex vivo use of gelatin according to any one of aspects 1 to 6 or a hydrogel according to aspect 7 for manufacturing a biological construct such as a tissue or an organ, or a part thereof, a coating, a scaffold, or a controlled release dosage form.

Aspect 15: Use of gelatin according to any one of aspects 1 to 6 or a hydrogel according to aspect 7 as a bio-ink or bio-resin.

The invention claimed is:

1. A gelatin modified with a methacryloyl group or an acryloyl group, having a lipopolysaccharide content of less than 100 EU/g, less than 50 EU/g, less than 20 EU/g, less than 10 EU/g, less than 5 EU/g, less than 2 EU/g, or less than 1 EU/g, and comprising less than 30 ppm of a methacrylic acid or an acrylic acid, wherein the methacrylic acid or the acrylic acid content is determined on a sample of the gelatin dissolved in water, or comprising less than 100 ppm of a methacrylic acid or an acrylic acid, wherein the methacrylic acid or acrylic acid content is determined on a sample of the gelatin dissolved in 50 mM phosphate buffer, pH 9.5.

2. The gelatin according to claim 1, wherein said gelatin is a type A gelatin.

3. The gelatin according to claim 1, having a degree of methacrylamide substitution or acrylamide substitution between 20% and 100%, between 50% and 100%, or between 80% and 100%, and a degree of methacrylate substitution of less than 10%.

4. The gelatin according to claim 1, wherein said gelatin is further modified with an acetyl group or moiety, a phenol group or moiety, a thiol group or moiety, a norbornene group or moiety, a tetrazine group or moiety, an azide group or moiety, a furan group or moiety, or any combination thereof.

5. A hydrogel comprising:

a gelatin modified with a methacryloyl group or an acryloyl group, wherein the gelatin modified with the methacryloyl group or the acryloyl group has a lipopolysaccharide content of less than 100 EU/g, less than 50 EU/g, less than 20 EU/g, less than 10 EU/g, less than 5 EU/g, less than 2 EU/g, or less than 1 EU/g, and comprises less than 30 ppm of methacrylic acid or acrylic acid, wherein the methacrylic acid or the acrylic acid content is determined on a sample of the gelatin dissolved in water, or comprises less than 100 ppm of a methacrylic acid or an acrylic acid, wherein the methacrylic acid or acrylic acid content is determined on a sample of the gelatin dissolved in 50 mM phosphate buffer, pH 9.5; and a cross-linking agent.

6. A film comprising a hydrogel according to claim 5.

7. A pharmaceutical composition comprising the gelatin of claim 1.

8. A bio-ink or a bio-resin comprising the gelatin of claim 1.

9. A pharmaceutical composition comprising the hydrogel of claim 5.

10. A bio-ink or a bio-resin comprising the hydrogel of claim 5.

* * * * *